(12) United States Patent
Darazs

(10) Patent No.: US 8,670,994 B2
(45) Date of Patent: Mar. 11, 2014

(54) METHOD AND SYSTEM FOR PROVIDING INFORMATION TO PHYSICIANS

(76) Inventor: Deborah L. Darazs, Morris, IL (US)

( * ) Notice: Subject to any disclaimer, the term of this patent is extended or adjusted under 35 U.S.C. 154(b) by 0 days.

(21) Appl. No.: 13/282,448

(22) Filed: Oct. 26, 2011

(65) Prior Publication Data

US 2012/0101844 A1 Apr. 26, 2012

(51) Int. Cl.
*G06Q 10/00* (2012.01)

(52) U.S. Cl.
USPC .................................. 705/2; 705/3; 600/300

(58) Field of Classification Search
USPC .......................................... 705/2–3; 600/300
See application file for complete search history.

(56) References Cited

U.S. PATENT DOCUMENTS

| | | | | |
|---|---|---|---|---|
| 6,063,028 | A  * | 5/2000 | Luciano | 600/300 |
| 2002/0029157 | A1* | 3/2002 | Marchosky | 705/3 |
| 2002/0165737 | A1* | 11/2002 | Mahran | 705/3 |
| 2002/0169635 | A1* | 11/2002 | Shillingburg | 705/2 |

* cited by examiner

*Primary Examiner* — Lena Najarian
(74) *Attorney, Agent, or Firm* — Miller, Matthias & Hull LLP

(57) ABSTRACT

A group of medical specialists reviews an up-to-date body of medical knowledge and, based on its review, selects a subset of that knowledge as being important enough to merit prompt dissemination to the medical community. The selected subset of medical knowledge is then input into a computer system where it can then be accessed by physicians over a computer network. A physician may, for example, access the system before, during or after a patients visit so that he/she can have the most up-to-date information regarding how to best advise the patient. In effect, the group of medical specialists acts as a single voice of authority on which the medical community can rely.

3 Claims, 3 Drawing Sheets

METHOD AND SYSTEM FOR PROVIDING INFORMATION TO PHYSICIANS

TECHNICAL FIELD OF THE INVENTION

The invention relates generally to providing medical information over a network and, more particularly, to providing pre-screened medical information to physicians over a network

BACKGROUND

Every day, the body of human medical knowledge grows with the addition of new discoveries and advances in patient care. It is, therefore, very challenging for the average physician to keep up with his or her specialty. Additionally, between keeping office hours, making hospital rounds, managing the flow of insurance paperwork, and participating in staff meetings, physicians have little time to read medical journals. In contrast, the average patient now has access to medical information through the Internet and through various media outlets, and, given enough time, can potentially be more up-to-date on his or her particular illness than the treating physician.

DETAILED DESCRIPTION

The invention is generally directed to a method and system for providing information to physicians, in which a group of medical specialists reviews an up-to-date body of medical knowledge and, based on its review, selects a subset of that knowledge as being important enough to merit prompt dissemination to the medical community. The selected subset of medical knowledge is then input into a computer system where it can then be accessed by physicians over a computer network. A physician may, for example, access the system before, during or after a patient's visit so that he/she can have the most up-to-date information regarding how to best advise the patient. In effect, the group of medical specialists acts as a single voice of authority on which the medical community can rely.

The interaction between the system and the physician may take a variety of forms. For example, the physician (or health care worker or other person working for the physician) may look up the information using a keyword search, browse for the information using a series of links, or enter patient information such as height, weight, gender, age and symptoms into a diagnosis engine. The physician may then, if desired, print out some or all of the information for the patient to take home. The types of information maintained by the computer system may include a variety of topics, such as recent breakthroughs in drug therapy, current test studies in their implication for the patient, new surgical techniques, or new findings regarding diet.

In various embodiments of the invention, the computer system includes an diagnosis engine that can receive information concerning a particular patient as input, access the subset of medical knowledge (as, for example, selected by the group of medical specialists), and provide, as an output, information that will assist a physician in treating the patient. A physician (or health care worker or other person working for the physician) may, for example, interactively provide the symptoms and test results as inputs to the system. The system then analyzes the inputs using the most up-to-date medical knowledge and provides a recommendation to the physician.

Figure 1:
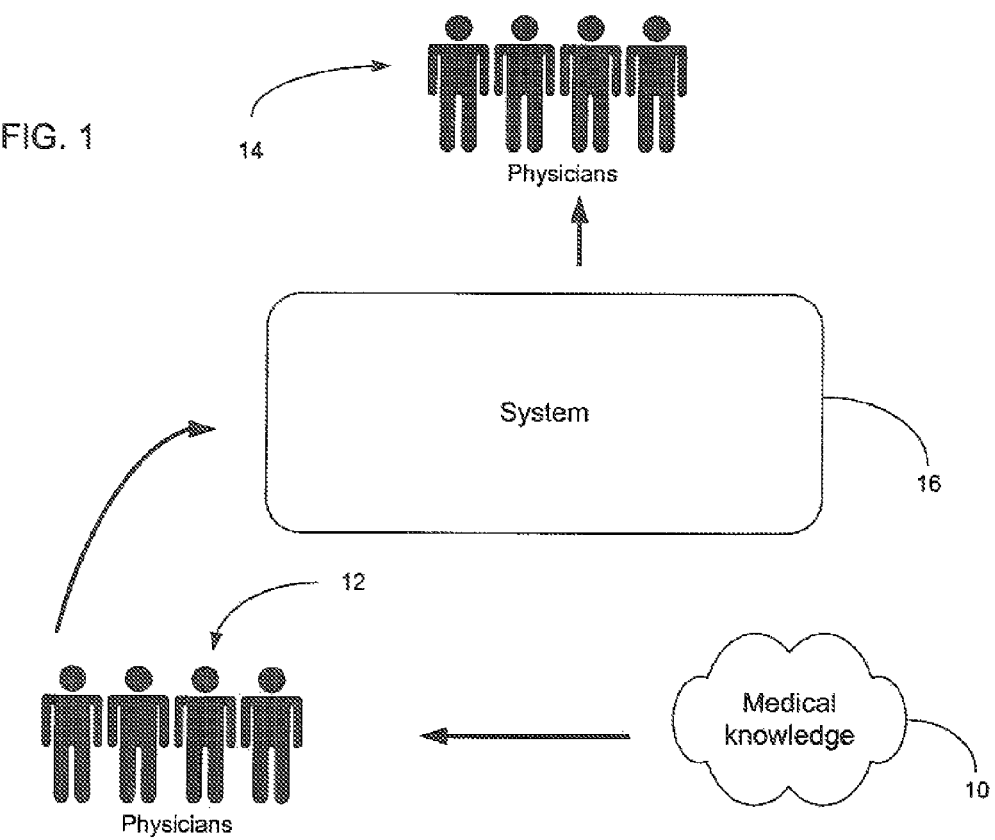
FIG. 1 shows the general flow of data that occurs in an embodiment of the invention.

The general flow of data that occurs according to an embodiment of the invention is described with reference to FIG. 1. In FIG. 1, a body 10 of medical knowledge is represented by a cloud. The medical knowledge may be obtained from a variety of sources including, for example, hospitals, universities, research institutions and pharmaceutical companies. The body 10 of medical knowledge may include one or more of the following: information regarding diseases, information regarding patient treatment, health information, diet information, information regarding medical research, write-ups of patient studies, write-ups of drug trials, published articles from medical journals, write-ups of government studies and write-ups of university research. Those portions of the body 10 of medical knowledge that are written down on paper, electronically, or in some other medium, will be referred to collectively herein as the body of medical literature.

A first group of physicians, generally labeled 12, is made up of recognized medical specialists and will be referred to hereinafter as the board of directors or "board" for short. The board 12 reviews the body 10 of medical knowledge and selects which subset of that body should be disseminated to the medical community, which is represented by a second group of physicians, generally labeled 14. The subset selected by the board 12 of physicians is entered into a computer system, generally labeled 16. The second group of physicians 14 can then access the system 16 to get the latest information regarding medical diagnosis and treatment of patients.

Referring again to FIG. 1, an example of how the board 12 is created and what sources of information it uses to determine what needs to be entered into the system 16 will now be described. The board 12 is created by obtaining the participation of a number of leading physicians. Although there are a variety of possible configurations for the board 12, according to an embodiment of the invention, the board 12 is made up of about 100 leading physicians, including physicians from every major medical field in the United States. Selecting which physicians are to be members of the board 12 may involve a variety of considerations. For example, a physician may be chosen based on one or more of the following: the hospitals with which the physician is associated, the universities with which the physician is associated, the research institutions with which the physician is associated, the physician's reputation, a physician's position at an institution (for example, a physician who is a head of a hospital might be preferable to a physician who is not), and the studies that the physician has authored. Many of these considerations relate to how much access the physician has to the latest research in the physician's field. The better the physician's access, the quicker the physician can identify important developments and have those developments entered into the system 16.

Figure 2:
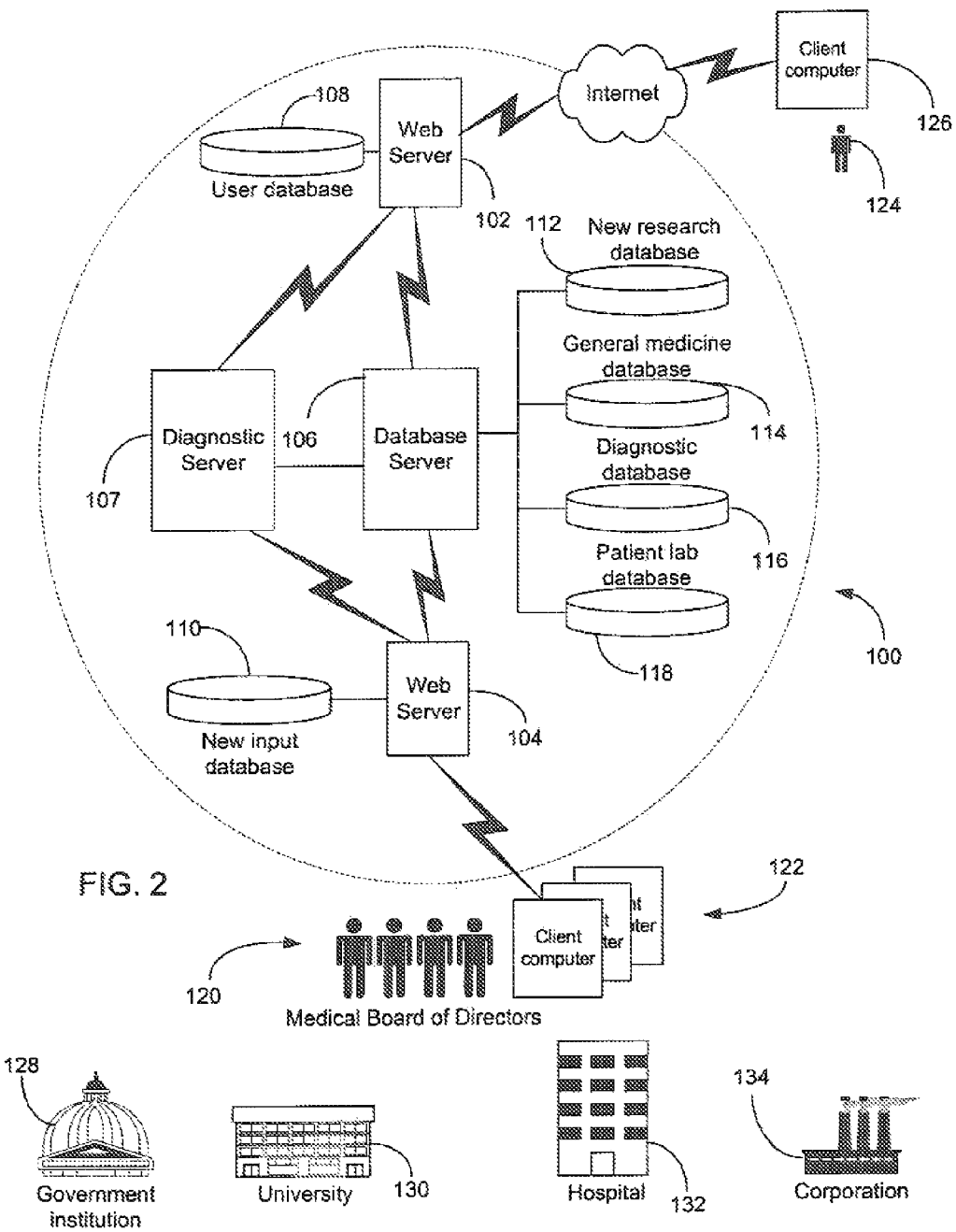
FIG. 2 shows an example of a system configured according to an embodiment of the invention.

Referring to FIG. 2, an example of a system configured according to an embodiment of the invention will now be described. The system, generally labeled 100, includes a first web server 102, a second web server 104, a database server 106 and a diagnostic server 107. Each of the first and second web servers 102 and 104 are communicatively linked to the database server 106 and to the diagnostic server 107. The diagnostic server 107 is communicatively linked to the database server 106. The web server 102 has access to a user database 108. The user database 108 contains information regarding users who are permitted to access the system 100. The database server 106 has access to a variety of medical databases including a new research database 112, a general medicine database 114, a diagnostic database 116 and a patient lab database 118. A user 124 communicates with the first web server 102 through a client computer 126. The user 124 may be a physician or someone working for a physician. A medical board 120 of directors, who are all licensed physicians of various medical specialties, receives input from a variety of sources, including a government institution 128, a university 130, a hospital 132 and a corporation 134 (which may be public or private). The members of the medical board 120 select which information should be put into the computer system 100 based on their years of experience and knowledge of their respective fields. For example, the decision as to which new studies, if any, on heart attack risk factors should be put into the system 100 is made by one or more leading cardiologists that serve on the medical board 120. The information is entered into the system 100 via one or more client computers 122, which transmit the information to the web server 104. The web server 104 temporarily stores the information in an input database 110 and, after properly formatting the information, transmits the information to the database server 106. The database server 106 then stores the information in one or more of the databases 112-118 as is appropriate.

Figure 3:
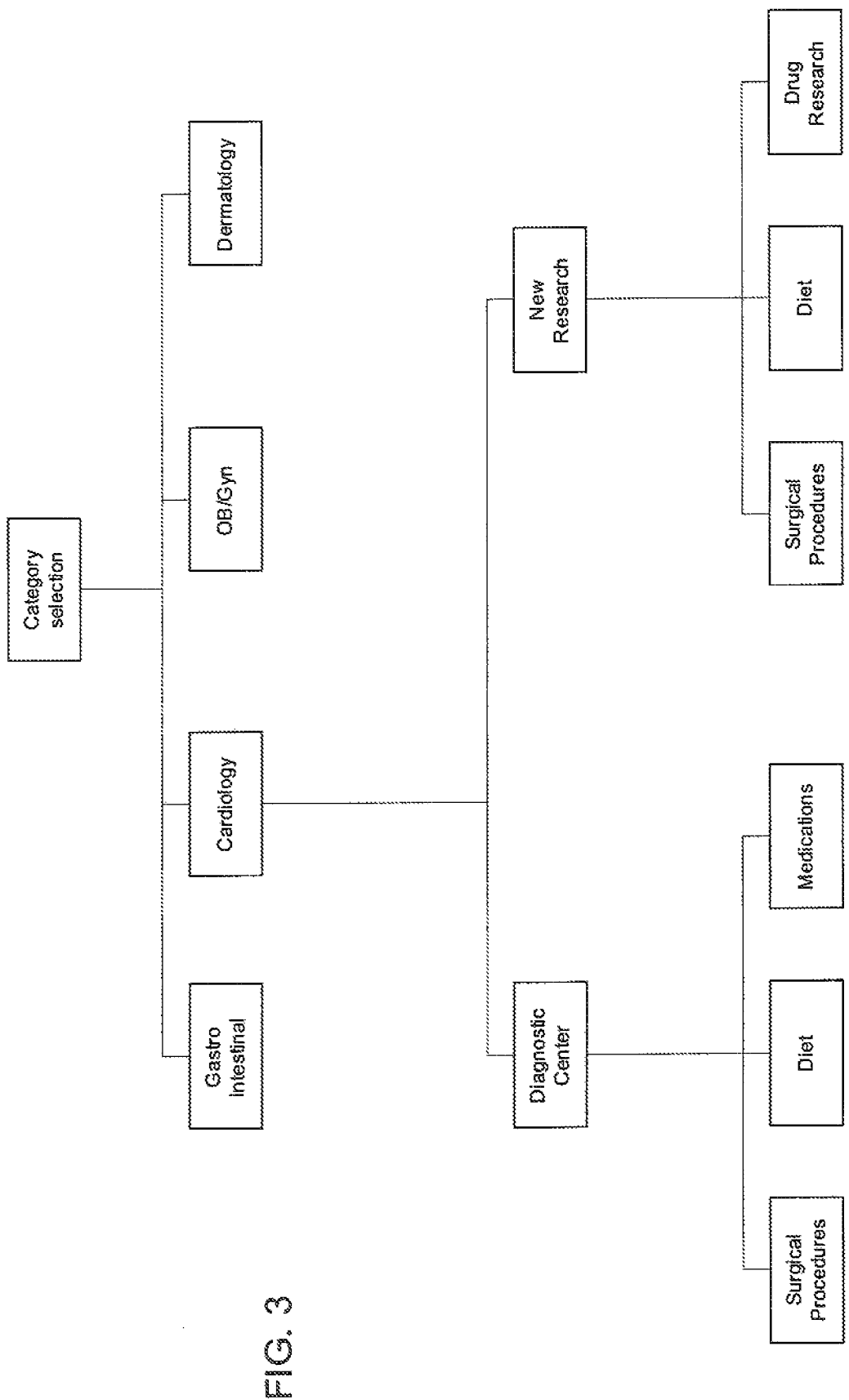
FIG. 3 is a diagram showing potential categories from which a user might choose in an embodiment of the invention.

When the user 124 wishes to avail of the system 100, the user 124 contacts the system 100 through the client computer 126 and the web server 102. The web server 102 authenticates the user 124 based on information in the user database 108. Examples of the types of information contained in the user database 108 include usernames and passwords. Once the user 124 is authenticated, the user 124 is presented with web-based interface that allows the user 124 to select one or more categories of medical information that the user 124 is able to access. The medical information categories may be organized in a variety of ways. A partial example of an organization of medical categories that may be shown to the user 124 through the web-based interface is shown in FIG. 3. As can be seen in FIG. 3, the user makes an initial selection among the categories of gastro-intestinal, cardiology, ob/gyn and dermatology. If the user 124 selects cardiology, the user 124 is then prompted to choose between a Virtual "diagnostic center" for diagnosing the cause of patient problems, and a "new research" category for finding out the results of recent medical studies. The diagnostic center category has three sub-categories—surgical procedures, diet and medications. The new research category also has three sub-categories—surgical procedures, diet and drug research. If the user 124 selects the diagnostic center then, according to some embodiments of the invention, an interactive communication session ensues between the system 100 and the user, in which the user inputs information about a particular patient and the computer system attempts to provide guidance as to how to diagnose and treat the patient. The communication session may occur in real-time, or there may be a delay between inputs and responses.

An example of how information is acquired and entered into the system 100 will now be described with reference to FIG. 2. In this example, one of the physicians of the medical board 120 is the head of the cardiology department of the hospital 132. That physician learns that clinical trials of a new drug, produced by the corporation 134, have shown that the drug can significantly reduce the occurrence of heart attacks in at-risk patients. The physician may also know of other similar clinical trials that are in progress using other drugs, but determines that the drug produced by the private corporation 134 currently represents the best hope for at-risk patients. Based on this judgment, and with the express or implied agreement of the rest of the medical board 120, the physician has one of his staff log on to the system 100 via one of the client computers 122 and enter information regarding the new drug. The information soon makes its way into the new research, database 112. The user 124, who is an internist working, at a hospital clinic, has a patient who is at risk for having a heart attack. The user 124 decides to log on to the system 100 via the client computer 126, and find out if there are any new drugs that might help the patient. The user 124 goes through a series of web pages, and arrives at a web page for "Cardiology—New research: Drug research" (as shown in the diagram of FIG. 3). The user 124 then studies the information, prints out a portion of the information for the patient, and advises the patient to switch to the new drug once it gets approved by the Food and Drug Administration (FDA).

Referring again to FIG. 2, an example of how the system 100 may be used to provide advice to a physician on diagnosing and treating a particular patient will now be described. In this example, it is assumed that, very recently, the university 130 discovered that a slightly elevated blood pressure, in combination with a slightly elevated white blood cell count, may indicate the presence of a newly discovered form of hepatitis. Furthermore, it is assumed that a hepatologist on the medical board 120 of directors has already decided that this discovery is important and has made sure that the discovery was entered into the diagnostic database 116. The physician 124 interviews the patient and finds that the patient is suffering from general fatigue. The physician 124 orders a routine blood test. When the results come back, the physician reviews them, and finds that the patient's blood pressure and white blood cell count are slightly elevated, but still within what is considered to be a normal range. Just to double-check, however, the physician 124 logs on to the system 100 via the web server 102. The physician 124 then selects, via a user interface, an interactive diagnostic tool that executes on the diagnostic server 107. The physician 124 enters the relevant patient information into the client computer 126. The diagnostic server 107 interacts with the database server 106 to obtain the most up-to-date information from the diagnostic database 116, then asks the physician 124 a series of follow-up questions. After the physician 124 answers the follow up questions, the diagnostic server 107 responds with a recommendation that the physician 124 check for the new form of hepatitis and, possibly, a link to an article regarding the newly discovered form of hepatitis.

It can thus be seen that a new and useful method and system for providing information to physicians has been provided. In view of the many possible embodiments to which the principles of this invention may be applied, it should be recognized that the embodiments described herein with respect to the drawing figure is meant to be illustrative only and should not be taken as limiting the scope of invention. For example, those of skill in the art will recognize that the elements of the illustrated embodiments shown in software may be implemented in hardware and vice versa or that the illustrated embodiments can be modified in arrangement and detail without departing from the spirit of the invention. Therefore, the invention as described herein contemplates all such embodiments as may come within the scope of the following claims and equivalents thereof.

I claim:

1. A method for assisting physicians and their licensed supervised healthcare workers in assessment and treatment of a patient's medical condition, the method being executed via a medical information platform that stores and processes medical information, the method comprising:

receiving, from a physician or licensed supervised healthcare worker at a first web server from a client computer over a computer network, an input of at least one or more symptoms of the patient;

receiving at a diagnostic server computer the one or more symptoms, as well as information from a database server computer linked to the diagnostic server computer and providing current medical information from a plurality of informational databases, the informational databases including at least a first informational database providing new research information, wherein the new research information is selected by a medical board from a plurality of sources including a government institution, a university, a hospital and a corporation, a second informational database providing general medical information, a third informational database providing diagnostic information and a fourth informational database providing patient lab information, the diagnostic server computer further being in communication with a second web server gathering medical information from a new input database;

the diagnostic sever computer analyzing the received information by comparing the one or more input symptoms to symptom information found in the first, second, third and fourth informational databases to generate a patient diagnosis consistent with the new research information, general medical information, diagnostic information and patient lab information; and sending from the diagnostic server computer to the physician or licensed supervised healthcare worker at the client computer over the computer network, a recommendation regarding how to diagnose the patient.

2. The method of claim 1, further comprising updating the plurality of medical information databases using a subset of medical knowledge regarding the diagnosis and treatment of patients selected by a plurality of medical specialists representing a plurality of respective medical specialties and/or subspecialties.

3. The method of claim 1, wherein the receiving, analyzing and sending steps are performed real-time in an interactive communication session with the health care worker.

* * * * *